United States Patent
Nakamura (10) Patent No.: US 8,480,613 B2
(45) Date of Patent: Jul. 9, 2013

(54) GAS MIST PRESSURE BATH SYSTEM

(75) Inventor: Shoichi Nakamura, Higashichikuma-gun (JP)

(73) Assignees: ACP Japan Co., Ltd., Tokyo (JP); Nakamura, Shoichi (Individual), Higashichikuma-Gun, Nagano (JP)

( * ) Notice: Subject to any disclaimer, the term of this patent is extended or adjusted under 35 U.S.C. 154(b) by 348 days.

(21) Appl. No.: 12/736,428

(22) PCT Filed: Dec. 9, 2009

(86) PCT No.: PCT/JP2009/070607
§ 371 (c)(1),
(2), (4) Date: Oct. 7, 2010

(87) PCT Pub. No.: WO2010/067821
PCT Pub. Date: Jun. 17, 2010

(65) Prior Publication Data
US 2011/0028889 A1 Feb. 3, 2011

(30) Foreign Application Priority Data

Dec. 10, 2008 (JP) ................. 2008-314676
Dec. 10, 2008 (JP) ................. 2008-314677

(51) Int. Cl.
*A61M 37/00* (2006.01)
(52) U.S. Cl.
USPC .............. 604/24; 604/23; 604/26; 604/27
(58) Field of Classification Search
USPC ........................ 604/23–24, 26, 27
See application file for complete search history.

(56) References Cited

U.S. PATENT DOCUMENTS

| | | | | |
|---|---|---|---|---|
| 2,486,297 | A | * | 10/1949 | Lederer ................ 239/280 |
| 7,276,051 | B1 | * | 10/2007 | Henley et al. ............ 604/304 |
| 2002/0007869 | A1 | * | 1/2002 | Pui et al. ................ 141/173 |
| 2006/0206051 | A1 | * | 9/2006 | Hamilton ................ 604/24 |

FOREIGN PATENT DOCUMENTS

| | | |
|---|---|---|
| JP | H07-171189 | 7/1995 |
| JP | 2005-205163 | 8/2005 |
| JP | 2006-026022 | 2/2006 |
| JP | 2007-014482 | 1/2007 |
| JP | 2007-181720 | 7/2007 |

* cited by examiner

*Primary Examiner* — Kevin C Sirmons
*Assistant Examiner* — Edelmira Bosques
(74) *Attorney, Agent, or Firm* — Manabu Kanesaka (57) ABSTRACT

The invention is to provide a gas mist pressure bath system, which is possible to control the amount of gas and liquid, pressure and others, and cause a gas mist to be absorbed through a skin and mucous membrane of a human living-body under an optimum condition, in which a mist is prepared by pulverizing and dissolving carbon dioxide or oxygen or a mixed gas of carbon dioxide and oxygen and a liquid at a density of not less than a predetermined value, and the thus prepared gas mist is directly contacted to the skin and mucous membrane of the living-body, the gas mist pressure bath system comprises a gas supply means 11, a liquid supply means 21, a gas mist supply means 31 for generating and supplying the gas mist prepared by blowing off gas supplied from the gas supply means into the liquid supplied from the liquid supply means 21, and the living body cover member 41 of covering the skin and mucous membrane of the living-body and forming a space of sealing the gas mist inside thereof, and the gas mist pressure bath system causes the gas mist within the living body cover member 41 to contact the skin and mucous membrane of the living-body at pressure of not less than a predetermined value.

19 Claims, 11 Drawing Sheets

GAS MIST PRESSURE BATH SYSTEM

RELATED APPLICATIONS

The present application is National Phase of International Application No. PCT/JP2009/070607 filed Dec. 9, 2009, and claims priorities from, Japanese Applications No. 2008-314676 filed Dec. 10, 2008 and No. 2008-314677 filed Dec. 10, 2009, the disclosure of which are hereby incorporated by reference herein in its entirety.

TECHNICAL FIELD

The present invention relates a gas mist pressure bath system, in which a mist (called as "gas mist" hereafter) is prepared by pulverizing and dissolving carbon dioxide or oxygen or a mixed gas (called as "gas" hereafter) of carbon dioxide and oxygen and a liquid, and the thus prepared gas mist is directly contacted to a skin and mucous membrane of a human living-body at pressure of not less than a predetermined value, thereby to improve a gas absorption efficiency into the skin and mucous membrane.

BACKGROUND ART

It has conventionally been known that carbon dioxide (carbonic acid anhydride: $CO_2$, called as "carbon dioxide" hereafter) has both properties of being not only soluble in water (water-soluble) but also soluble in fat (fat-soluble) and if, therefore, only contacting the skin and mucous membrane of the living-body being as mixed with water and fat, carbon dioxide penetrates under a subcutaneous layer and expands blood vessels around parts of penetrated carbon dioxide, and it works to improve a blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living-body works to release oxygen carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen and the cell becomes unable to receive oxygen. As is seen, carbon dioxide seems to be a waste product resulted from action of oxygen, however, it plays in fact very important roles in the human living-body.

Further, in recent times, oxygen of high density has also widely been known as effective in activity of metabolism, accelerating the blood circulation, fatigue recovery, or stability of blood pressure. Other than them, oxygen has disinfection or sterilization by oxidative effect.

As a prior art for causing carbon dioxide to be absorbed into the living body, a most broadly used technique is (1) a bathing agent issuing carbon dioxide in water. Throwing this bathing agent into hot water in a bathtub, it generates carbon dioxide by reacting acid and carbonate contained in the bathing agent, and dissolves in hot water. Carbon dioxide dissolved in hot water contacts the skin of a bathing person and penetrates under the subcutaneous layer to display physiological effects as above mentioned.

As a prior art for causing more carbon dioxide to contact the living body, (2) a carbon dioxide bathing device is known. This emits and disperses carbon dioxide in hot water and dissolves it at high density. When bathing in hot water dissolving carbon dioxide, the skin directly contacts it like the bathing agent.

A blood circulation accelerating device (for example, Patent Document 1) has now been disclosed, which (3) attaches a cover to a human living body on its one part to form a sealed space together with the surface of the human living body, and introduces carbon dioxide into the sealed space from a carbon dioxide supply means for carrying out a carbon dioxide bath.

Inventors of the present invention have proposed a carbon dioxide pressure bath device which is equipped with at least (4) the carbon dioxide supply means, a pressurizing means, and a covering material for covering the skin of the living body and causing carbon dioxide to contact the skin of the living body at pressure of not less than predetermined value.

As a prior art for causing oxygen to be absorbed into the living body, (5) a high density oxygen bathing device has been known. Being similar to the carbon dioxide bathing device, this emits and disperses carbon dioxide in hot water, in which taking a bath, the skin is caused to directly contact oxygen.

CITATION LIST

Patent Documents

Patent Document 1: Japanese Patent Application Publication No. 07-171189

SUMMARY OF INVENTION

Problems to be Solved by the Invention

However, each of the above prior arts (1), (2) and (5) dissolves carbon dioxide or oxygen in hot water when taking the bath, and causes carbon dioxide or oxygen to be absorbed into the skin of the living body. Accordingly, they were involved with difficult points of using only when taking the bath. In addition, since carbon dioxide is easily dissolved in water, and even if much consuming it, an absorption rate is not high.

On the other hand, the above prior arts (3) and (4) cause carbon dioxide to directly contact the living body, and comparing with the prior arts (1) and (2), effects are high and efficiency is good. But these have not optimized to control the amount or pressure of carbon dioxide to be introduced into the shielding member (cover) and the amount of the mist.

In view of the above mentioned problems, it is an object of the invention to provide a gas mist pressure bath system which is possible to control the amounts of the gas and liquid, pressure and others, and cause the gas mist to be absorbed through the skin and mucous membrane of the human living-body under an optimum condition.

Means for Solving the Problem

For solving the above mentioned problems, the present invention is to provide a gas mist pressure bath system, in which a mist (called as "gas mist" hereafter) is prepared by pulverizing and dissolving carbon dioxide or oxygen or a mixed gas (called as "gas" hereafter) of carbon dioxide and oxygen and a liquid at a density of not less than a predetermined value, and the thus prepared gas mist is directly contacted to the skin and mucous membrane of the living-body, and the present gas mist pressure bath system comprises a gas supply means, a liquid supply means, a gas mist supply means for generating and supplying the gas mist prepared by blowing off the gas supplied from the gas supply means into the liquid supplied from the liquid supply means, and a living body cover member for covering the skin and mucous membrane of the living-body and formed with a space of sealing inside thereof the gas mist supplied from the gas mist supply means, and is characterized by causing the gas mist within the living body cover member to contact the skin and mucous membrane of the living-body at pressure of not less than a predetermined value.

By the way, the invention refers it as "pulverizing and dissolving" to pulverize liquid into fine liquid drops, and cause to contact the gas (carbon dioxide, or oxygen, or the mixed gas of carbon dioxide and oxygen).

Herein, more desirably, the above mentioned gas mist pressure bath system of the invention is further provided with a sensor for measuring supplying conditions of gas, liquid and the gas mist, and control means for controlling supplies of the gas, liquid and the gas mist based on the measuring values of the sensor.

In addition, the above gas mist pressure bath system is desirably further provided with a pressurizing means for pressurizing the living-body cover member.

The control means may supply the gas mist intermittently into the living-body cover member to perform an interval pressurization (pulse pressurization) thereon. Otherwise, the pressurizing means may pressurize the living-body cover member intermittently to perform the interval pressurization (pulse pressurization) thereon.

It is optimum that the above mentioned liquid is any one or plural combination of water, ionic water, physiological salt solution, ozone water, purified water or sterilized water. This liquid further contains any one or plural combination of menthol, vitamin E, vitamin C derivative, retinol, anesthetic, cyclodextrin, photocatalyst, complex of photocatalyst and apatite, hyaluronic acid, coenzyme Q10, seed oil, propolith, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, carcinostatic substance, anti-hyper tensive agent, cosmetic agent, or trichogen.

Preferably, the liquid is supplied into the gas mist supply means under a condition of being heated. Grain sizes of the gas mist supplied from the gas mist supply means to the living-body cover member are suitably not more than 10

The control means preferably holds pressure at 1.02 to 2.5 air pressure in the living-body cover member when taking the gas mist bath.

There may be provided a charge supply means for supplying an electric charge to the mist from the gas mist supply means. At this time, the charge is preferably a minus charge.

Desirably, the gas mist supply means has a gas mist supply pipe for supplying the gas mist into the inside of the living-body cover member, and this gas mist supply pipe has a filter for removing liquid drops attached to a pipe inside.

Further, a whole or one of the gas mist supply pipe is suitably composed of a cornice shaped pipe, and this gas mist supply pipe is provided with a check valve.

In addition, the gas mist supply mouth of the living-body cover member is also provided at its supply mouth with the check valve.

The gas mist supply means has a storage for storing the liquid and the gas mist, and the storage is shaped in dome of convex having inside a curved face toward an upper portion and is formed with a gas mist exhaust portion at the dome shaped top.

Further, the gas mist supply means has a storage for storing the liquid and the gas mist, and the storage has desirably one or plurality of pored plates for refining the gas mist.

The control means desirably stops the gas from the gas supply means when the pressurizing value within the living-body cover member is higher than a predetermined value.

Advantageous Effect of the Invention

According to the gas mist pressure bath system of the invention, since it is possible to control the amount and pressure of the gas mist in the living-body cover by the control device, the gas mist bath can be always taken under the best condition.

Further, pressurization into the living-body pressure bath cover is easy, and a skin-pass breath of the gas can be carried out more efficiently.

DESCRIPTION OF EMBODIMENTS

In the following description, explanations will be made to embodiments of this invention, referring to the attached drawings.

First Embodiment

Figure 1:
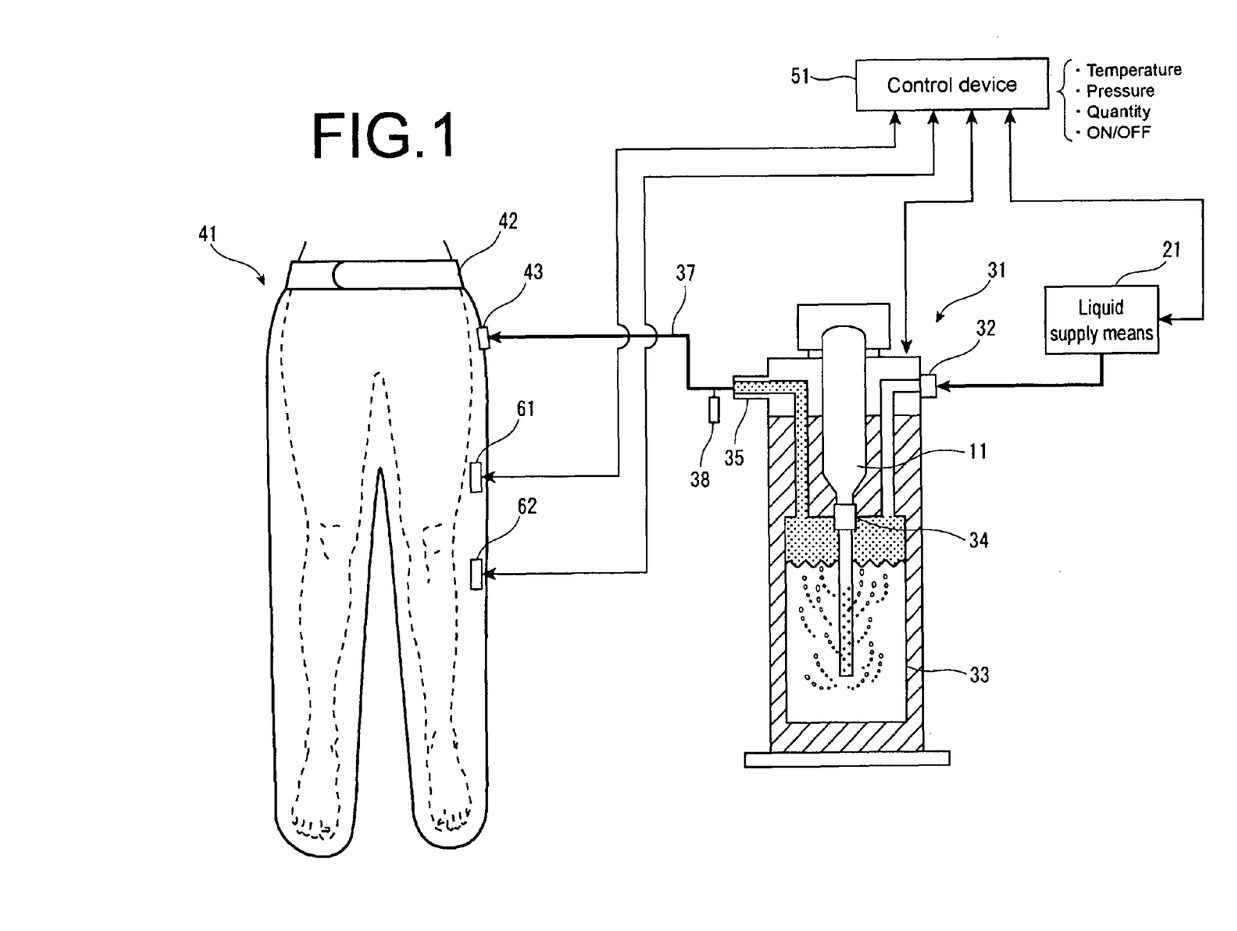
FIG. 1 A generally schematic view of the gas mist pressure bath system depending on a first embodiment of the invention.

FIG. 1 is the generally schematic view of the gas mist pressure bath system depending on the first embodiment of the invention. As shown in this view, the gas mist pressure bath system of this embodiment comprises the gas supply means 11, the liquid supply means 21, the gas mist supply device 31 for generating and supplying under pressure the gas mist prepared by blowing off the gas (carbon dioxide or oxygen or the mixed gas of carbon dioxide and oxygen) into the liquid, the gas mist pressure bath cover 41 formed with a space for sealing the supplied gas mist therein, and the control device 51 for generating and controlling to supply the gas mist.

The gas supply means 11 is composed of, for example, a gas bomb, and supplies the gas to the gas mist supply device 31, thereby to supply the gas mist into the living-body pressure bath cover 41. Omitting illustration, a regulator may be furnished for adjusting gas pressure, and the gas supply means 11 may be disposed with a heater for heating gas or a thermometer for controlling temperatures.

The liquid supply means 21 is composed of a pump or the like and supplies water to the gas mist supply device 31. As the liquid, it is suitable to use water, ionic water, physiological salt solution, ozone water, purified water or sterilized water. Further, these liquids may contain medicines useful to user's diseases or symptoms. For the medicines, enumerated are, for example, anti-allergic agent, anti-inflammatory agent, anti-febrile, anti-fungus agent, anti-influenza virus, carcinostatic substance, anti-hyper tensive agent, cosmetic agent, or tri-chogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflammatory agent, pain-killing, anesthetic, and immunity. Otherwise, the liquids may be added with ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate. In addition, high density carbonate spring may be added (as examples organic components, sulfate, carbonate, sodium dichloroisocyanurate).

The liquid supply means 21 is desirably furnished with a heater (not shown) heating the liquid (for example, heating to a hot water of around 40° C.) or a thermometer (not shown).

Figure 2:
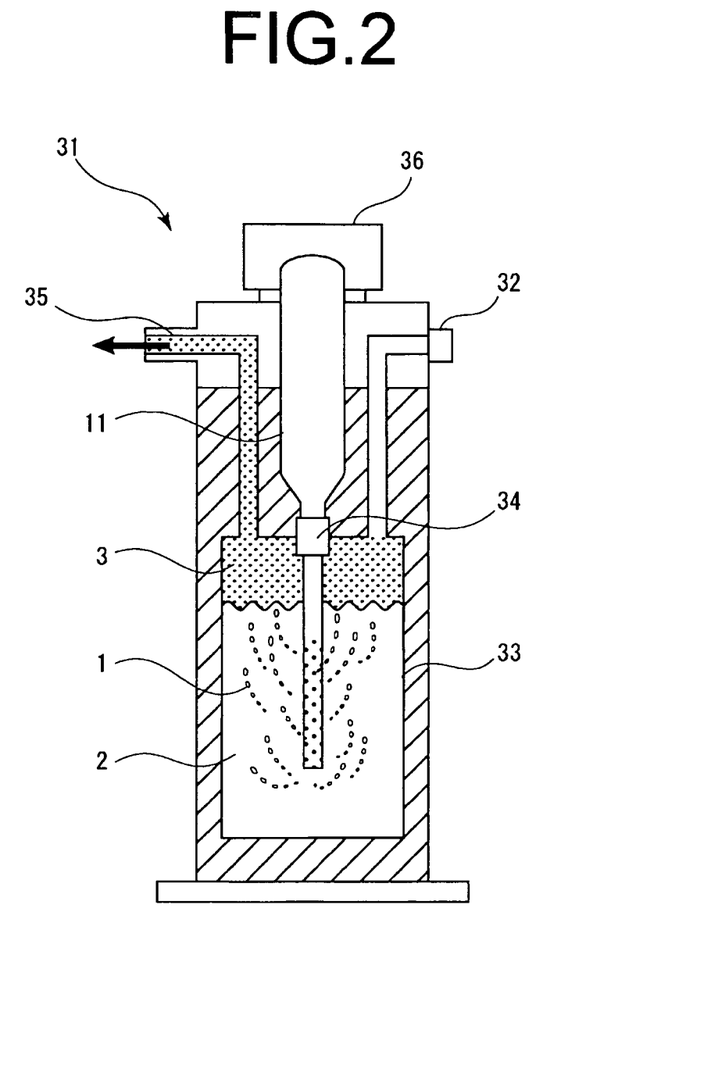
FIG. 2 A typical view showing one example of the gas mist supply device in the gas mist pressure bath system depending on the invention.

The gas mist supply device 31 is a device which stores inside the liquid supplied from the liquid supply means 21 and blows off at high pressure gas from the gas supply means into the gas mist supply device 31, thereby to generate the gas mist prepared by pulverizing and dissolving gas and liquid, and supplies under pressure the gas mist into the living-body pressure bath cover 41. FIG. 2 shows one example of the gas mist supply device 31. As shown in FIG. 2, the gas mist supply device 31 comprises a liquid inlet 32 for injecting the liquid inside, a liquid tank (storage part) 33 for storing the liquid 2 injected from the liquid inlet 32, a gas supply port 34 having inside a needle of opening the gas supply means (herein, a cartridge type small gas bomb) 11 and for blowing off gas 1 into the liquid 2 in the liquid tank 33, a gas mist exhaust port 35 for exhausting the gas mist occurring by blowing off the gas 1 into the liquid 2, and a cap 36 for securing the gas bomb 11 and concurrently urging the gas bomb 11 to the gas port 34.

For generating the gas mist 3, the liquid 2 of around 40 to 70° C. is in advance poured from the liquid inlet 32 into the liquid tank 33, and the liquid inlet 32 is closed. Next, the gas bomb 11 is set on the gas port 34, and when the cap 36 is tightened, the gas bomb 11 is brought down and opened by the needle furnished inside of the gas port 34. Then, the gas 1 is spouted and blown off into the liquid 2. At this time, in particular, in the vicinity of the upper surface of the liquid 2 in the liquid tank 33, the liquid 2 and the gas 1 are pulverized and dissolved, whereby the gas mist 3 is generated. Grain sizes of the supplied mist is desirably fine, and concretely, being less than 10 μm is optimum.

The generated gas mist 3 is supplied into the living-body pressure bath cover 41 via a gas mist supply pipe 37 from the gas mist exhaust port 35. The gas mist supply pipe 37 is connected to a supply mouth 43 of the living-body pressure bath cover 41, and is desirably furnished with a filter 38 for removing liquid drops attached to the inside of the pipe. Although not illustrating, the gas mist supply pipe 37 is provided with a check valve for checking back-flow of the gas mist.

Figure 3:
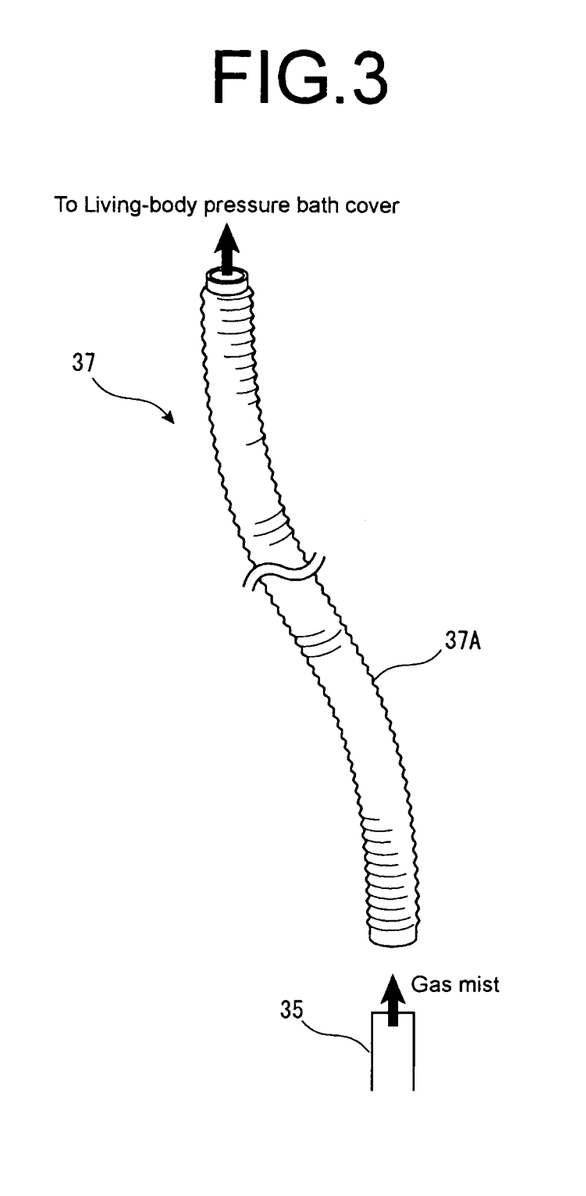
FIG. 3 A typical view showing one example of the gas mist supply pipe used to the gas mist pressure bath system depending on the invention.

Further, as shown in FIG. 3, preferably, the gas mist supply pipe 37 is overall or partially composed of a soft cornice shaped pipe 37A of a large diameter. If composing with such a corniced pipe 37A, the gas mist supply pipe 37 is freely bent and may be expanded so that the user is not restricted in action. Even if the gas mist flowing in the gas mist supply pipe 37 becomes gradually liquefied, the liquid can be removed through concaves and convexes of the cornice.

As to the liquid tank 33, although showing the structure of substantially cylindrical shape and an upper face being level as FIG. 1, a dome shape is enough having inside a convex and curved face toward an upper portion. In this case, the gas mist exhaust port 35 is placed on a top part of the dome shape. With this shape, the mist contacts the upper portion of the inside wall of the gas mist supply device 33 to prevent from turning liquid and dropping to the bottom of the gas mist supply device 33, so that the gas mist can be more stored.

Figure 4:
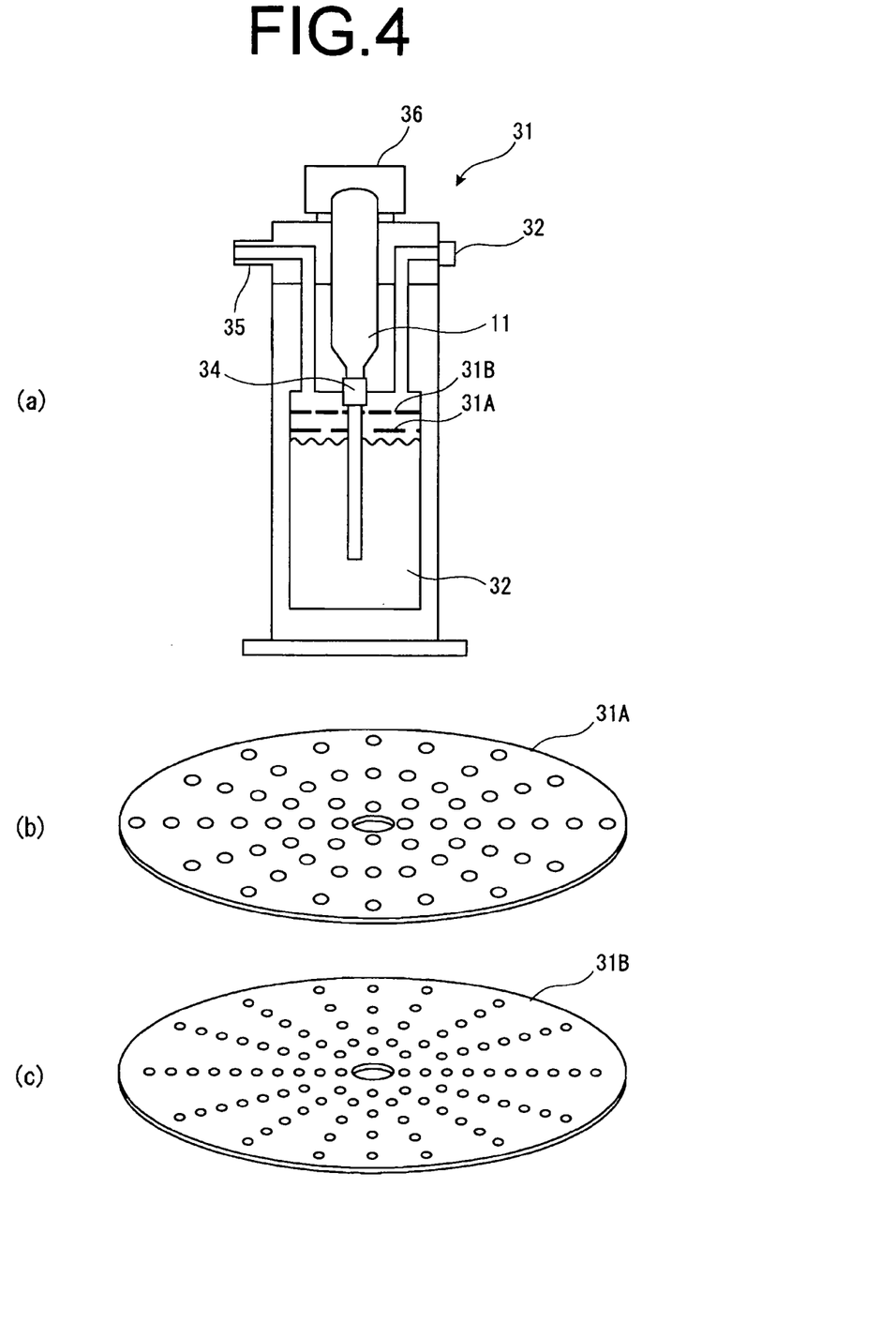
FIG. 4 Typical views showing examples of plates arranged in the gas mist supply device of the gas mist pressure bath system depending on the invention.

The liquid tank 33 may be, as shown in FIG. 4(a), furnished inside with one or plural sheets of plates 31A, 31B (in FIG. 4, as the example, two sheets). The plates 31A, 31B are, as shown in FIG. 4(b), (c), formed with plural pores respectively, and the generated gas mist is further refined by passing through the pores. Then, with respect to the upper plate 31B and the lower plate 31A, the diameters of the upper plate 31B are preferably smaller than those of the lower plate 31A.

The gas supply means 11 employs herein the cartridge type small gas bomb, and instead, no matter occurs about using of a business type large gas bomb.

The living-body pressure bath cover 41 may form a space for covering the skin and mucous membrane of the living body (herein, as the example, a lower extremity), and the gas mist and the gas inside. The living-body pressure bath cover 41 is composed of a pressure resistant, non-air permeable and non-moisture permeable material, and preferably, for example, the natural rubber, silicone rubber, polyethylene, poly propylene, polyvinylidene, polystylene, polyvinylacetate, poly vinyl chloride, polyamide resin, polytetrafluoroethylene. The living-body pressure bath cover 41 has a supply port 43 for introducing the gas mist inside thereof. The supply port 43 is inside provided with the check valve for checking back flow of the gas mist. The living-body pressure bath cover 41 may be provided with an opening mouth or a valve for exhausting gas and the gas mist. The pressure control may be carried out manually, but as later mentioned, desirably automatically by a control device 51 together with supply control of gas and the gas mist. A safety valve (recess valve) may be provided for automatically opening a valve when the inside of the living-body pressure bath cover 41 becomes more than a constant pressure.

The living-body pressure bath cover 41 is inside installed with a manometer 61 for measuring an inside pressure. The control device 51 controls supply of the gas mist on the basis of measuring values of the manometer 61 for maintaining a pressure value within the living-body pressure bath cover 41 to be more than 1 air pressure (more preferably, around 1.02 to 2.5 air pressure). For example, the control device 51 controls or stops the supply of gas or the gas mist from the gas supply means 11 and the gas mist supply device 31, or exhausts the gas mist or gas from the living-body pressure bath cover 41. Further, the living-body pressure bath cover 41 is inside installed with a thermometer 62 for measuring an inside temperature within the living-body pressure bath cover 41. The control device 51 performs on-off of a heater installed in the liquid supply means 21 on the basis of measuring values of a manometer 62 for maintaining a predetermined temperature (for example, around 38° C.) bringing about warm bath effects within the living-body pressure bath cover 41.

The living-body pressure bath cover 41 has, around its opening, a stopper 42 for attaching to and detaching from the living body (herein, as the example, the lower extremities) and stopping leakage of the gas mist. The stopper 42 is suitably composed of, e.g., a stretching face fastener, or may have a sole string or rubber or their combination. For heightening a sealing property in the living-body pressure bath cover 41, the inside (that of the stopper 42) may have a material attaching to the user's skin. The adhesive material is preferably a visco-elastic gel of polyurethane or silicone rubber. Further, this adhesive material is detachably used and exchangeable each time or if viscosity becomes weak.

The control device 51 is composed of a computer having CPU, memory and display. This performs various kinds of controls such as on-off switch of the liquid from the liquid supply means 21; on-off switch of the heater; and on-off switch of supply of the gas mist from the gas mist supply device 31, in order to perform the gas mist pressure bath under an optimum condition. In particular, it is preferable to compose a structure, when the pressure value becomes a predetermined value, supplying of the gas from the gas supply means 11 is stopped.

For carrying out the gas mist pressure bath using the gas mist pressure bath system of the present embodiment, the living-body pressure bath cover 41 is secured to the living body (herein, as the example, the lower extremity) and closed. Then, the liquid of a specified amount is supplied from the liquid supply means 21 into the liquid tank 33 of the gas mist supply device 31. Subsequently, the gas bomb 11 is set to blow off the gas into the liquid, generate the gas mist, and supply it into the living-body pressure bath cover 41. The control device 51 carries out adjustments of supplying pressure, amount and temperature of the liquid and the gas. The inside of the living-body pressure bath cover 41 is controlled to be the optimum pressurized and heated conditions (around 1.02 to 2.5 air pressure and around 38° C.) in view of the measuring values of the manometer 61 and the thermometer 62, and when the control device 51 becomes the optimum condition, supply of the gas mist is once stopped, and under this condition the gas mist pressure bath is carried out.

The above mentioned explanation has been made with the example of the lower extremity of the living-body, and the invention is applicable to various parts. Then, the optimum gas mist pressure bath is performed using the living-body pressure bath cover 41 meeting object parts of the living-body.

Figure 5:
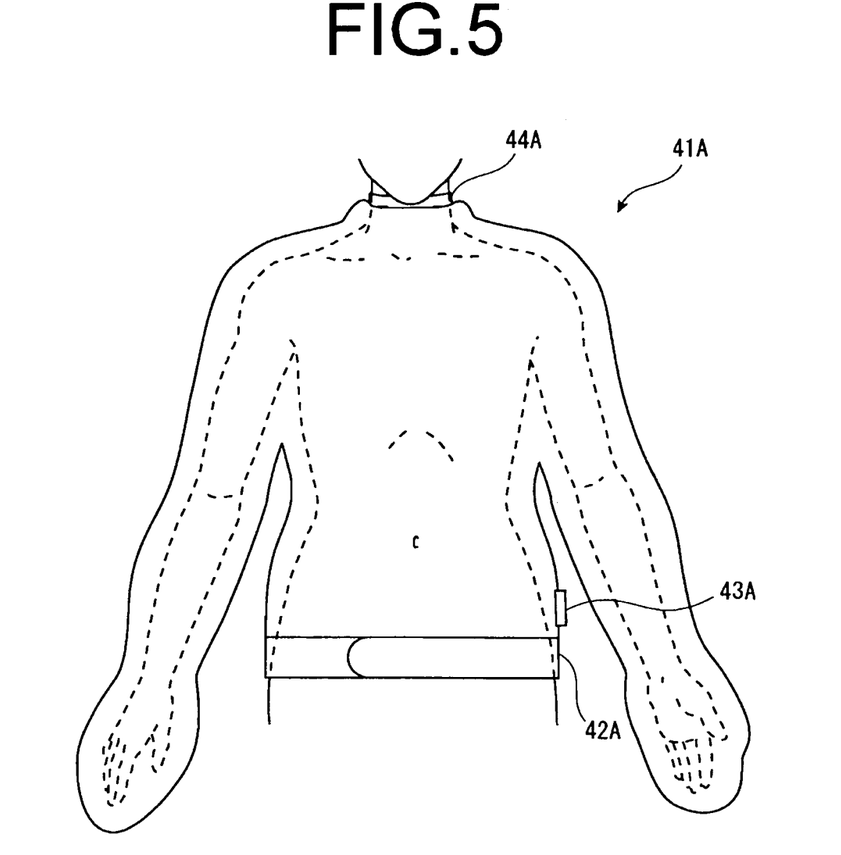
FIG. 5 A typical view showing a configuration example (No. 1) of the living-body cover of the gas mist pressure bath system depending on the first embodiment of the invention.
Figure 6:
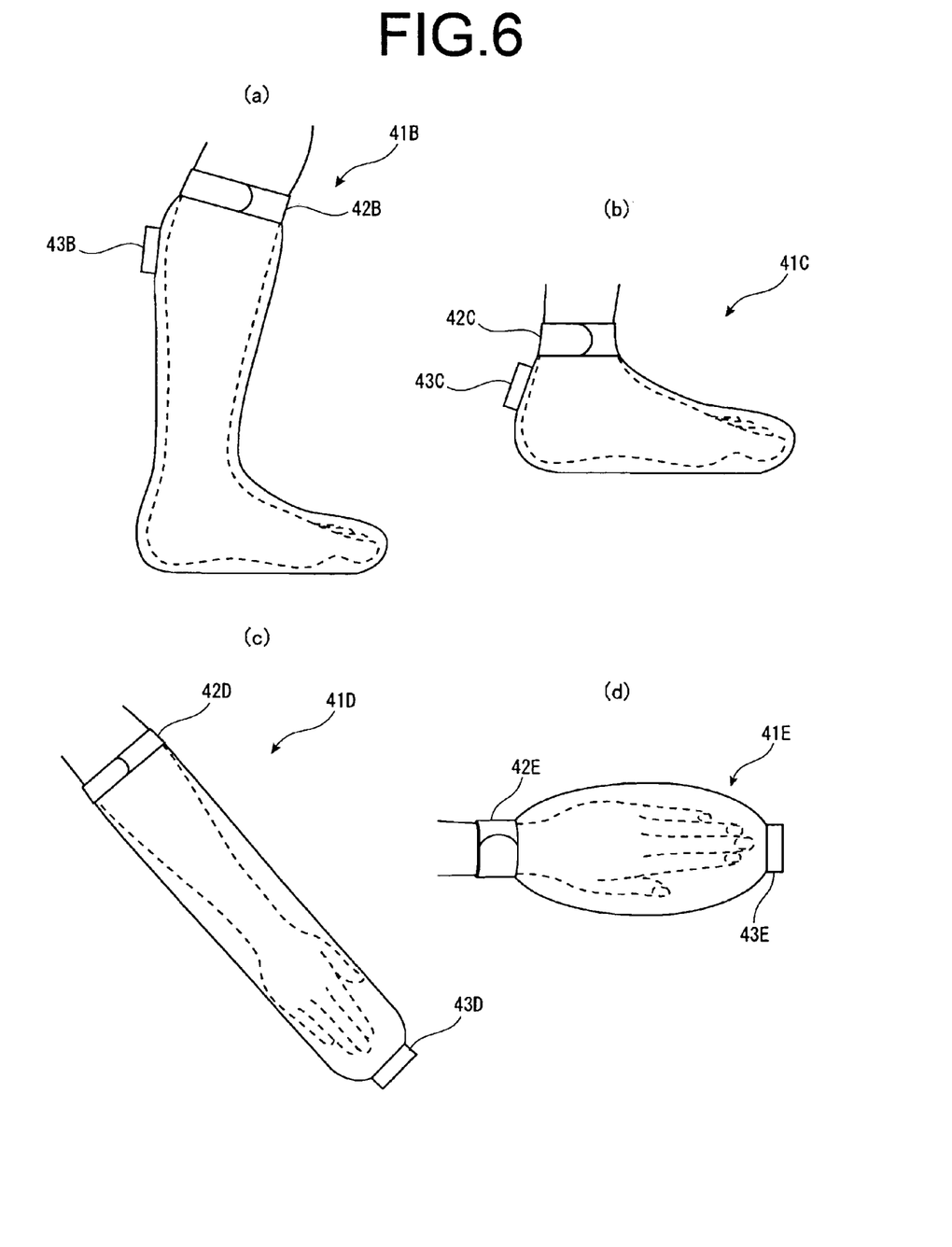
FIG. 6 A typical view showing a configuration example (No. 2) of the living-body cover of the gas mist pressure bath system depending on the first embodiment of the invention.
Figure 7:
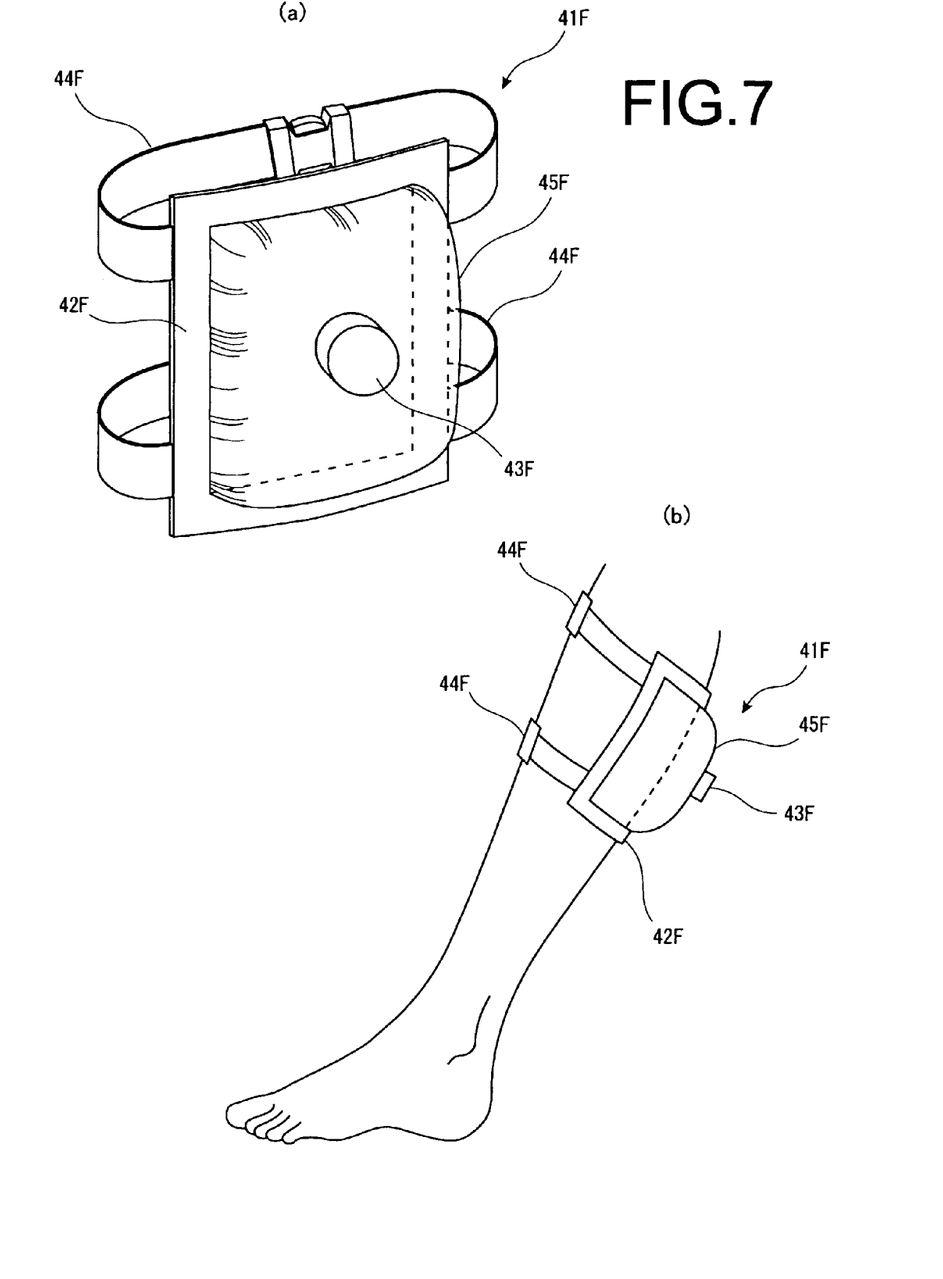
FIG. 7 A typical view showing a configuration example (No. 3) of the living-body cover of the gas mist pressure bath system depending on the first embodiment of the invention.

FIGS. 5 to 7 show the various shaped examples of the living-body pressure bath covers 41. At first, FIG. 5 shows the schematic view of the living-body pressure bath cover 41A for the upper half of the body. The living-body pressure bath cover 41A has a shape for wrapping the whole of the upper half of the body, and has a stopper 42A for attaching to and detaching from the living body and stopping leakage of the gas mist. A similar stopper 44A is formed around the opening of a neck 43A designates a supply mouth for introducing the gas mist and the gas inside.

FIG. 6 shows the various shaped examples of the living-body of the living-body pressure bath covers 41 for covering further limited parts of the living body. FIG. 6(a) is a living-body pressure bath cover 41B for one-side lower extremity (lower part under a knee) of the living body. The living-body pressure bath cover 41B has a stopper 42B at its opening part and a supply mouth 43B for introducing the gas mist inside. FIG. 6(b) is a living-body pressure bath cover 41C for a foot of the living-body. The living-body pressure bath cover 41C has a stopper 42C at its opening part and a supply mouth 43C for introducing the gas mist inside thereof. FIG. 6(c) is a living-body pressure bath cover 41D for an arm of the living body. The living-body pressure bath cover 41D has a stopper 42D and a supply mouth 43D for introducing the gas mist inside. FIG. 6(d) is a living-body pressure bath cover 41E for a hand of the living-body. The living-body pressure bath cover 41E has a stopper 42E and a supply mouth 43E for introducing the gas mist inside.

Further, FIG. 7 shows a patch shaped living-body pressure bath covers 41F. FIG. 7(a) is a view showing an outline of the patch shaped living-body pressure bath covers 41F. FIG. 7(b) is a view showing an external appearance when attaching the patch shaped living-body pressure bath covers 41F to the living body (herein, lower extremity of the living body). The living-body pressure bath covers 41F is composed of a cover part 45F for covering the skin and mucous membrane of the living-body, a stopper 42F provided at the margin of the cover part 45F and directly attached to the skin and mucous membrane of the living-body, a supply mouth 43F for supplying the gas mist into a space defined by the cover 45F and the stopper 42F, and fasteners 44F made of belts or strings for fastening the cover part 45F to the living body.

In regard to the living-body pressure bath covers 41, other than the examples shown in FIGS. 5 to 7, various shapes may be assumed. In sum, as far as forming spaces for sealing the gas mist inside, any shapes are sufficient. An exhaust mouth may be formed for exhausting the gas mist from the inside of the living-body pressure bath covers 41. In addition, the invention may be applied not only to the human living body but to animals.

In addition, since pressurization in the gas mist pressure bath heightens the effects by pressurizing in pulsing at predetermined interval, the control device 51 may supply the gas mist into the living body pressure bath cover 41 intermittently at fixed rhythm. As to the pressurizing interval at such a case, if synchronizing with pulsations, the effects are more heightened.

Second Embodiment

Figure 8:
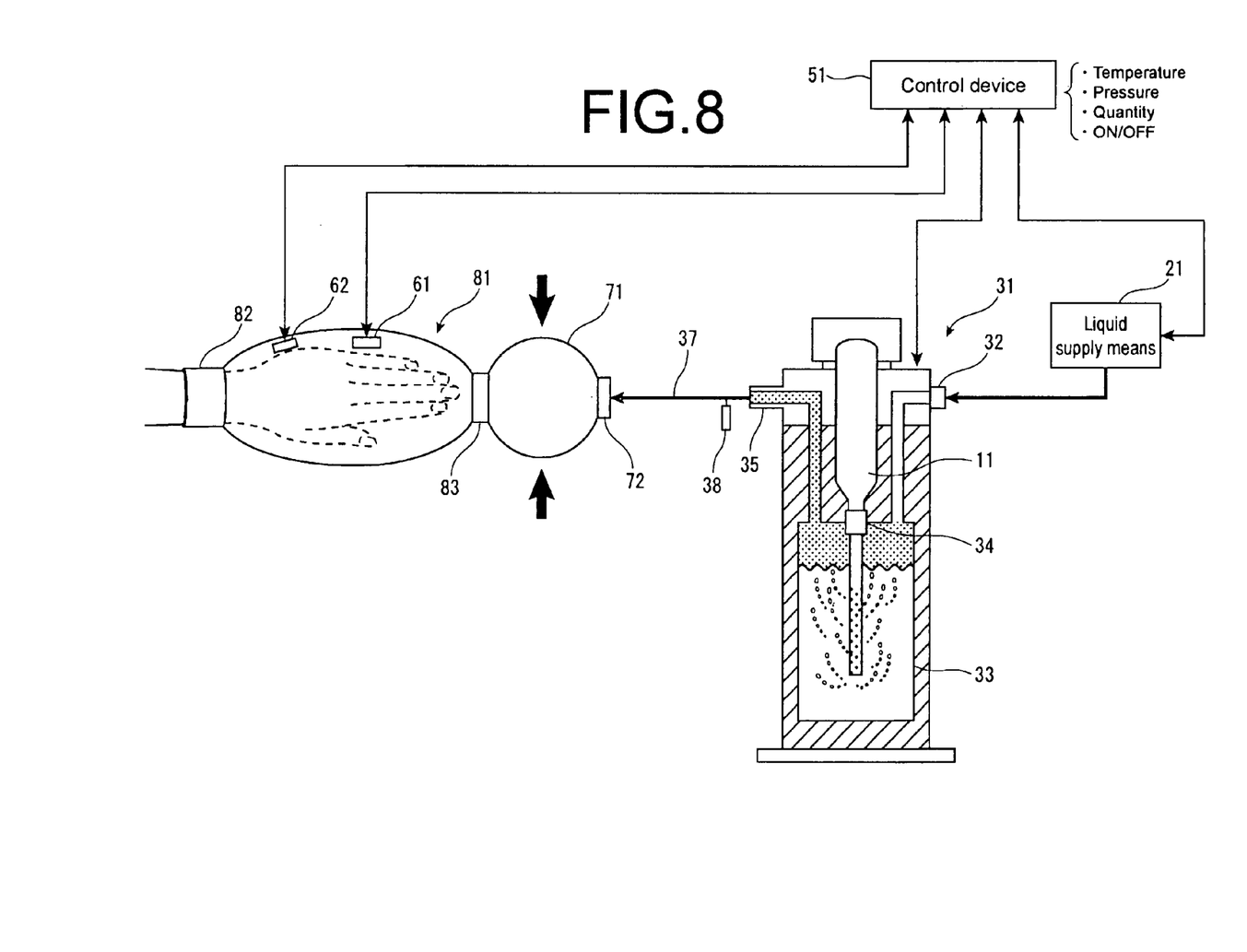
FIG. 8 A generally schematic view of the gas mist pressure bath system depending on a second embodiment of the invention.

FIG. 8 is the whole schematic view of the gas mist pressure bath system depending on the second embodiment of this invention. This embodiment will explain the gas mist pressure bath system further having a pressurizing means for simplifying pressurization within the living-body pressure bath cover. As to the same parts as those of the first embodiment shown in FIG. 1, the same numerals will be given, and detailed explanation will be omitted.

As shown in FIG. 8, the gas mist pressure bath system of this invention has a living-body pressure bath cover 81 forming a space into which the gas mist is sealed, and a pressurizing part (gas storage) 71 connecting the living body pressure bath cover 81 for pressurizing therein.

The living body pressure bath cover 81 has almost the same structure of the living body pressure bath cover 41 of the first embodiment, and has a stopper 82 and a gas mist and gas supply mouth 83, provided herein that the supply mouth 83 is connected to the pressurizing part 71. By the way, the example hereof illustrates the living body pressure bath cover 81 of a shape for covering a hand of the human living body.

The pressurizing part 71 is the hollow gas storage connecting the living body pressure bath cover 81 for pressurizing therein. The pressurizing part 71 is connected to the supply mouth 83 of the living body pressure bath cover 81 and has also a supply mouth 72 for itself from which the gas mist is supplied therein. The supply mouth 72 of the pressurizing part 71 is also provided with the check valve for checking back-flow of the gas mist. After storing the gas mist in the pressurizing part 71, if pressurizing as crushing the pressurizing part 71 as showing with arrows, since the gas mist in the pressurizing part 71 is exhausted as escaping into the living body pressure bath cover 81, the inside of the living body pressure bath cover 81 can be pressurized.

The pressurizing part 71 may be structured as pressing manually, and mechanically by controlling the control means 51 using a driving device. As mentioned above, pressurization in the gas mist pressure bath heightens effects by performing an interval pressurization in pulse, and so the pressurizing part 71 may be pressed intermittently. The pressurizing interval heightens effects by synchronizing with pulsation of pulse.

For carrying out the gas mist pressure bath using the gas mist pressure bath system of the present embodiment, the living-body pressure bath cover 81 is secured to the living body (herein, as the example, the hand of the human living body) and closed. Then, the liquid of a specified amount is supplied from the liquid supply means 21 into the liquid tank 33 of the gas mist supply device 31. Subsequently, the gas bomb 11 is set to blow off the gas into the liquid, generate the gas mist, and supply it into the living-body pressure bath cover 41. The control device 51 carries out adjustments of supplying pressure, amount and temperature of the liquid and the gas. The control device 51 is controlled to be at an optimum temperature within the living-body pressure bath cover 81 in view of the measuring values of the manometer 62 (for example, around 38° C.). When the gas mist of the optimum amount are stored in the living-body pressure bath cover 81 and the pressurizing part 71, the pressurizing part 71 is pressurized as crushed. Thereby, the gas mist in the pressurizing part 71 is exhausted into the living-body pressure bath cover 81, and the inside of the living-body pressure bath cover 81 is pressurized moderately (around 1.02 to 2.5 air pressure) and the gas mist pressure bath is carried out.

As having mentioned in the first embodiment, since the living-body pressure bath cover 81 is applied to various parts of the living body, many shapes may be used, provided in this embodiment that shapes (size) must be easily pressurized in the pressurizing part 71. This substantially depends on the dimension of the pressurizing part 71. Actually, so far as pressurizing means are any one, the pressurizing part 71 is desirably compact as not large spaces, and accordingly, the living-body pressure bath cover is also desirably applied to comparatively compact objects (covering limited parts of the living body).

Figure 9:
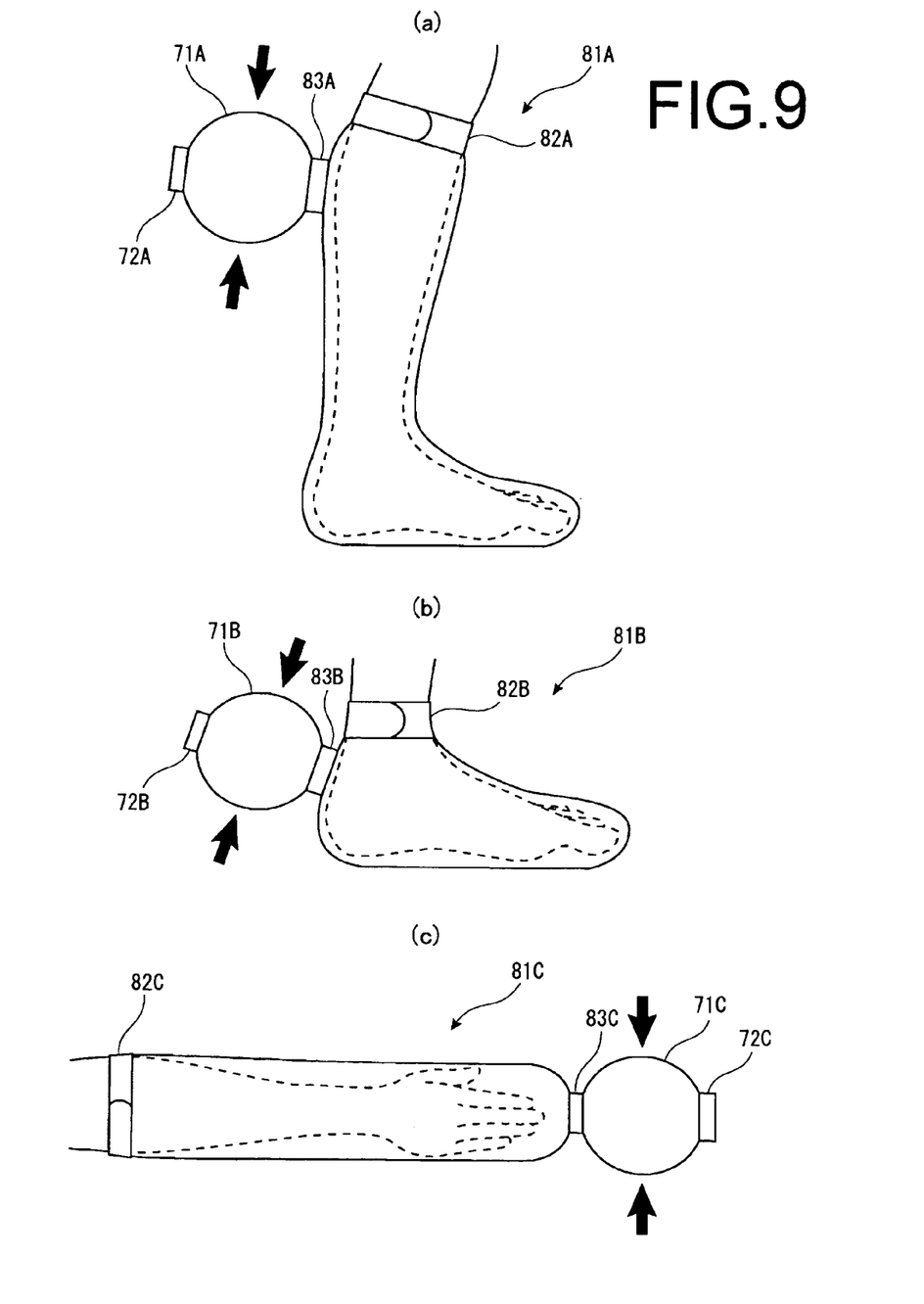
FIG. 9 A typical view showing a configuration example (No. 1) of the living-body cover of the gas mist pressure bath system depending on the second embodiment of the invention.
Figure 10:
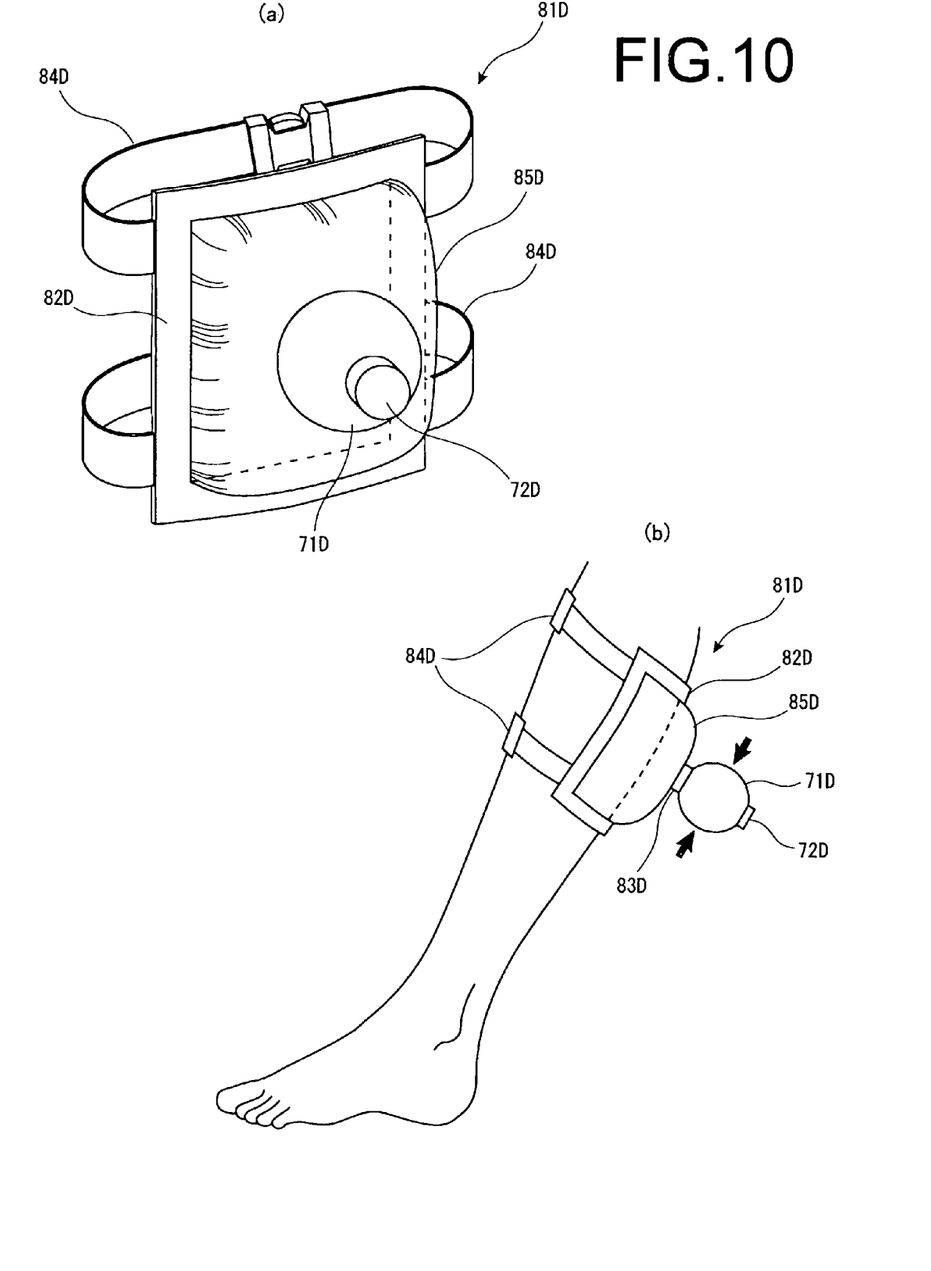
FIG. 10 A typical view showing a configuration example (No. 2) of the living-body cover of the gas mist pressure bath system depending on the second embodiment of the invention.

FIGS. 9 and 10 show the examples of shapes of the living-body pressure bath cover 81 and the pressurizing part 71 connected thereto. FIG. 9(a) is a living-body pressure bath cover 81A for one-side lower extremity (lower part under a knee) of the living body. The living-body pressure bath cover 81A has a stopper 82A at its opening part and a supply mouth 83A for introducing the gas mist inside. The supply mouth 83A is connected to the pressurizing part 71 and through a supply mouth 72A of a pressurizing part 71A, the gas mist is supplied into the living-body pressure bath cover 81A. FIG. 9(b) is a living-body pressure bath cover 81B for a foot of the living body. The living-body pressure bath cover 81B has a stopper 82B at its opening part and a supply mouth 83B for introducing the gas mist inside. The supply mouth 83B is connected to a pressurizing part 71B, and through a supply mouth 72B of a pressurizing part 71B, the gas mist is supplied into the living-body pressure bath cover 81B. FIG. 9(c) is a living-body pressure bath cover 81C for an arm of the living-body. The living-body pressure bath cover 81C has a stopper 82C at its opening part and a supply mouth 83C for introducing the gas mist inside. The supply mouth 83C is connected to a pressurizing part 71C, and through a supply mouth 72C of a pressurizing part 71C, the gas mist is supplied into the living-body pressure bath cover 81C.

FIG. 10 shows a patch shaped living-body pressure bath covers 81D. FIG. 10(a) is a view showing an outline of the patch shaped living-body pressure bath covers 81D. FIG. 10(b) is a view showing an external appearance when attaching the patch shaped living-body pressure bath covers 81D to the living body (herein, lower extremity of the living body). The living-body pressure bath covers 81D is composed of a cover part 85D for covering the skin and mucous membrane of the living-body, a stopper 82D provided at the margin of the cover part 85D and directly attached to the skin and mucous membrane of the living-body, a supply mouth 83D for supplying the gas mist into a space defined by the cover 85D and the stopper 82D, and fasteners 84D made of belts or strings for fastening the cover part 85D to the living body. The supply mouth 83D is connected to a pressurizing part 71D, and through a supply mouth 72D of the pressurizing part 71D, the gas mist is supplied into the living-body pressure bath cover 81D.

An exhaust mouth may be formed for exhausting the gas mist from the inside of the living-body pressure bath cover 81. In addition, the invention may be applied not only to the human living body but to animals.

In the above embodiment, the pressurizing part 71 is the hollow gas storage connected to the living-body pressure bath cover 81, and so far as materials of easily pressurizing as crushing externally the living-body pressure bath cover 81 itself, any materials are sufficient.

Third Embodiment

Figure 11:
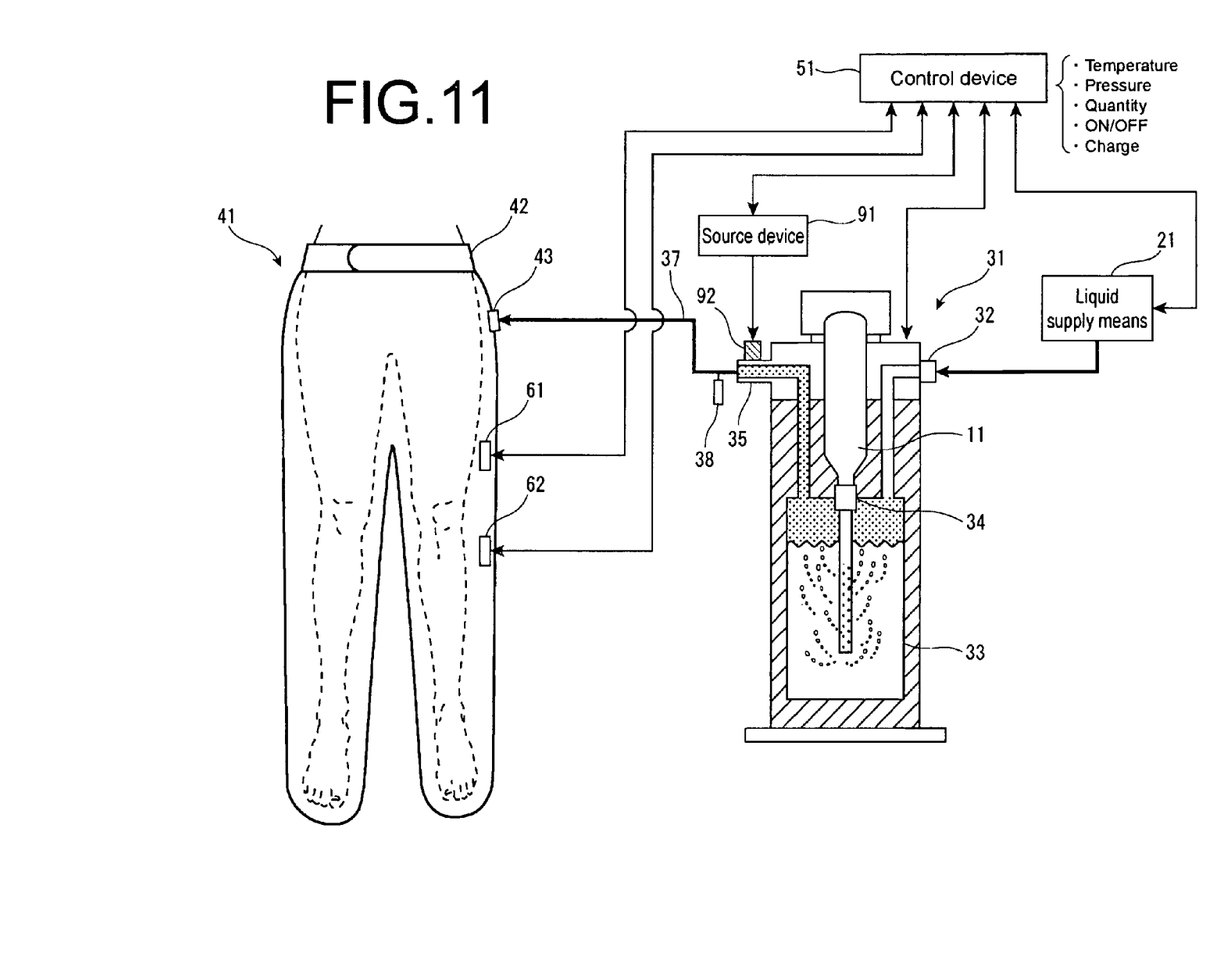
FIG. 11 A generally schematic view of the gas mist pressure bath system depending on a third embodiment of the invention.

FIG. 11 is the whole schematic view of the gas mist pressure bath system depending on the third embodiment of this invention. This embodiment will explain the gas mist pressure bath system further having a means for charging generated mist. As to the same parts as those of the first embodiment shown in FIG. 1, the same numerals will be given, and detailed explanation will be omitted.

As shown in FIG. 11, the gas mist pressure bath system of this invention is arranged with an electrode 92 at the gas mist exhaust mouth 35 of the gas mist supply device 31. The electrode 92 is connected to a source device 91, and the control device 51 sets voltage values and performs on-off control.

The electrode 92 supplies charge (minus charge is desirable) when exhausting the mist generated by the gas mist supply device 31 from the gas mist exhausting mouth 35. Thereby, the mist turns out charged so that adhesion to a charged material can be heightened. For example, if heightening adhesion to the skin and the mucous membrane of the living body, an effect of increasing absorption of gas by the mist is further heightened, and if the mist contains the above mentioned medicines, penetration into the skin and the mucous membrane can be accelerated.

For carrying out the gas mist pressure bath using the gas mist pressure bath system of the present embodiment, the living-body pressure bath cover 41 is secured to the living body (herein, as the example, the lower extremity of the human living body) and sealed. Then, the liquid of a specified amount is supplied from the liquid supply means 21 into the liquid tank 33 of the gas mist supply device 31. Subsequently, the gas bomb 11 is set to blow off the gas into the liquid, and generate the gas mist. Then, the control device 51 controls pressure, the amount and temperature of supplying the liquid and gas, and turns on the source device 91 to supply charge to the mist. This is supplied to the living-body pressure bath cover 41 via the supply mouth 43. The control device 51 is controlled such that the inside of the living-body pressure bath cover 41 becomes an optimum pressurized and heated conditions (around 1.02 to 2.5 air pressure and around 38° C.) in view of the measuring values of the manometer 61 and the thermometer 62, and when becoming the optimum conditions, the supply of the gas mist is once stopped and under this condition the gas mist pressure bath is carried out.

With the structure as mentioned above, according to the gas mist pressure bath system of the present invention, it is possible to control the amount, pressure and other of the gas mist within the living-body pressure bath cover by the control device, and so the gas mist pressure bath can be always carried out under the optimum condition.

Further, pressurization into the living-body pressure bath cover is easy, the gas skin-pass absorption can be more efficiently performed.

The above explanation has been made to the embodiments of the invention, but the invention is not limited to such embodiments, and so far as not deviating from the subject matter of the invention, various kinds of embodiments are, of course, available.

INDUSTRIAL APPLICABILITY

Thus, the present invention relates to the gas mist pressure bath device, in which the gas mist is prepared by pulverizing and dissolving the gas and the liquid, and is caused to contact the skin and mucous membrane of the living-body for improving absorbing efficiency of gas into the skin and mucous membrane, and has an industrial applicability.

DESCRIPTION OF SYMBOLS

1: Gas,
2: Liquid,
3: Gas mist,
11: Gas supply means,
21: Liquid supply means,
31: Gas mist supply device,
32: Liquid inlet,
33: Liquid tank,
34: Gas port
35: Gas mist exhaust mouth,
36: Cap,
37: Gas mist supply pipe,
37A: Cornice shaped pipe,
38: Liquid drop removing filter,
41, 41A, 41B, 41C, 41D, 41E, 41F, 81, 81A, 81B, 81C, 81D: Living-body pressure bath cover,
42, 42A, 42B, 42C, 42D, 42E, 42F, 44A, 82, 82A, 82B, 82C, 82D: Stopper,
43, 43A, 43B, 43C, 43D, 43E, 43F, 83, 83A, 83B, 83C, 83D: Supply mouth,
44F: Fastener,
45F: Cover part,
51: Control device,
61: Manometer,
62: Thermometer,
71, 71A, 71B, 71C, 71D: Pressurizing part,
72, 72A, 72B, 72C, 72D: Supply mouth,
84D: Fastener,
85D: Cover part,
91: Source device, and
92: Electrode.

The invention claimed is:

1. A gas mist pressure bath system, in which a gas mist is prepared by pulverizing and dissolving a gas including carbon dioxide or oxygen or a mixed gas of carbon dioxide and oxygen, and a liquid at a density of not less than a predetermined value, and the gas mist is contacted to a skin and mucous membrane of a living-body, comprising:
a gas supply device having a gas bomb portion, and a nozzle portion extending from the gas bomb portion for supplying the gas,
a liquid supply device for supplying the liquid,
a gas mist supply device connected to the gas supply device and the liquid supply device, the gas mist supply device having a storage portion for storing the liquid, a space formed above the liquid in the storage portion, and at least one pored plate arranged in the space for refining the gas mist, wherein a part of the nozzle portion of the gas supply device is soaked in the liquid of the storage portion for generating the gas mist by blowing off the gas supplied from the nozzle portion of the gas supply device into the liquid stored in the storage portion, and
a living-body cover member for covering the skin and mucous membrane of the living-body and formed with a space of sealing the gas mist supplied from the storage portion through the at least one pored plate in the gas mist supply device therein,
wherein the gas mist within the living body cover member is caused to contact the skin and mucous membrane of the living-body at pressure of not less than the predetermined value.

2. A gas mist pressure bath system as set forth in claim 1, wherein the at least one pored plate comprises an upper plate and a lower plate apart from each other, each plate having pores therein so as to refine the gas mist; and a diameter of the pore of the upper plate is smaller than that of the lower plate, and the pores of the upper plate are placed out of alignment with those of the lower plate.

3. A gas mist pressure bath system as set forth in claim 2, wherein the gas mist supply device further comprises a gas mist exhaust pipe and a liquid inlet pipe, each pipe extending upwardly from an upper surface of the storage portion, and the gas supply device is housed between the gas mist exhaust pipe and the liquid inlet pipe in the gas mist supply device.

4. A gas mist pressure bath system as set forth in claim 3, further comprising a sensor for measuring supplying conditions of the gas, liquid and gas mist, and a control device for controlling supplies of the gas, liquid and gas mist based on a measuring values of the sensor.

5. A gas mist pressure bath system as set forth in claim 4, wherein the control device supplies the gas mist intermittently into the living-body cover member to perform an interval pressurization on the living-body cover member.

6. A gas mist pressure bath system as set forth in claim 4, wherein the control device controls a supply of the gas from the gas supply device or the gas mist from the gas mist supply device, and exhausts the gas or the gas mist from the living-body cover member such that the control device holds pressure at 1.02 to 2.5 atmospheric pressure in the living-body cover member, when taking a gas mist bath.

7. A gas mist pressure bath system as set forth in claim 4, wherein the control device stops the gas from the gas supply device when a pressurizing value within the living-body cover member is higher than a predetermined value.

8. A gas mist pressure bath system as set forth in claim 3, further with comprising a pressurizing device for pressurizing the living-body cover member.

9. A gas mist pressure bath system as set forth in claim 8 wherein the pressurizing device pressurizes the living-body cover member intermittently to perform the interval pressurization on the living-body cover member.

10. A gas mist pressure bath system as set forth in claim 3, wherein the liquid is supplied into the gas mist supply device under a condition of being heated.

11. A gas mist pressure bath system as set forth in claim 3, wherein grain sizes of the gas mist supplied from the gas mist supply device to the living-body cover member are not more than 10 μm.

12. A gas mist pressure bath system as set forth in claim 3, further comprising a charge supply device for supplying charge to the gas mist from the gas mist supply device.

13. A gas mist pressure bath system as set forth in claim 12, wherein the charge is a minus charge.

14. A gas mist pressure bath system as set forth in claim 3, wherein the gas mist supply device has a gas mist supply pipe for supplying the gas mist into the living-body cover member, and the gas mist supply pipe has a filter for removing liquid drops attached therein.

15. A gas mist pressure bath system as set forth in claim 3, wherein the gas mist supply device has a gas mist supply pipe for supplying the gas mist into the living-body cover member, and at least one of the gas mist supply pipe is composed of a cornice shaped pipe.

16. A gas mist pressure bath system as set forth in claim 3, wherein the gas mist supply device has a gas mist supply pipe, and the gas mist supply pipe is provided with a check valve.

17. A gas mist pressure bath system as set forth in claim 3, wherein the living-body cover member has a gas mist supply mouth and a check valve is formed therein.

18. A gas mist pressure bath system as set forth in claim 1, wherein the above mentioned liquid is at least one of water, ionic water, physiological salt solution, ozone water, purified water or sterilized water.

19. A gas mist pressure bath system as set forth in claim 18, wherein the above mentioned liquid further contains at least one of menthol, vitamin E, vitamin C derivative, retinol, anesthetic, cyclodextrin, photocatalyst, complex of photocatalyst and apatite, hyaluronic acid, coenzyme Q10, seed oil, propolith, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, carcino-static substance, anti-hypertensive agent, cosmetic agent, or trichogen.

\* \* \* \* \*